(12) United States Patent
Griffiths

(10) Patent No.: US 6,238,414 B1
(45) Date of Patent: May 29, 2001

(54) LAPAROSCOPIC INSTRUMENT WITH PARALLEL ACTUATED JAWS

(76) Inventor: Jerry R. Griffiths, 196 Plain St., Pembroke, MA (US) 02359

( * ) Notice: Subject to any disclaimer, the term of this patent is extended or adjusted under 35 U.S.C. 154(b) by 0 days.

(21) Appl. No.: 09/488,057

(22) Filed: Jan. 20, 2000

(51) Int. Cl.$^7$ .................................................. A61B 17/28
(52) U.S. Cl. .......................................... 606/205; 606/208
(58) Field of Search .................................... 606/205, 206, 606/207, 208, 50, 51, 52, 170, 167

(56) References Cited

U.S. PATENT DOCUMENTS

| | | | |
|---|---|---|---|
| 5,258,006 | * 11/1993 | Rydell et al. | 606/205 |
| 5,261,918 | * 11/1993 | Phillips et al. | 606/205 |
| 5,308,358 | 5/1994 | Bond et al. . | |
| 5,318,589 | 6/1994 | Lichtman . | |
| 5,368,606 | 11/1994 | Marlow et al. . | |
| 5,728,121 | 3/1998 | Bimbo et al. . | |
| 5,797,919 | * 8/1998 | Brinson | 606/207 |
| 5,853,412 | 12/1998 | Mayenberger . | |
| 6,090,109 | * 7/2000 | Lands et al. | 606/207 |

* cited by examiner

*Primary Examiner*—Kevin Truong
(74) *Attorney, Agent, or Firm*—D. Michael Burns

(57) ABSTRACT

A surgical instrument including a handle assembly, and end effector mechanism including jaws, an elongated shaft assembly having a longitudinal actuation rod linearly reciprocating within a hollow sheath, slidably connecting the handle assembly to the jaws. Jaws having first and second grasping members have a mechanically controlled linkage assembly enabling the jaws to be adapted such that they can only open in parallel relationship to each other. The linkage assembly having a pair of toggle links which are rotatively connected to a linear translation member to cause the jaws to open or close. The linkage assembly further having a pair of stabilizing links, which at one end are pivotally anchored to a non-reciprocal movement member, and at an opposite end interconnected with the jaws to maintain the opposing serrated grasping surfaces of the jaws in a parallel relationship to each other.

15 Claims, 10 Drawing Sheets

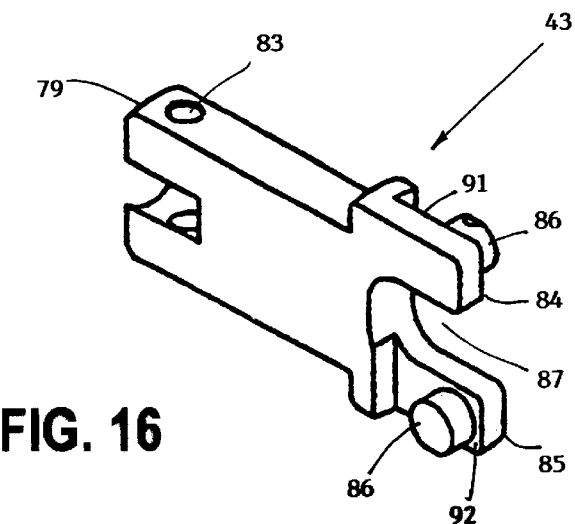
FIG. 16
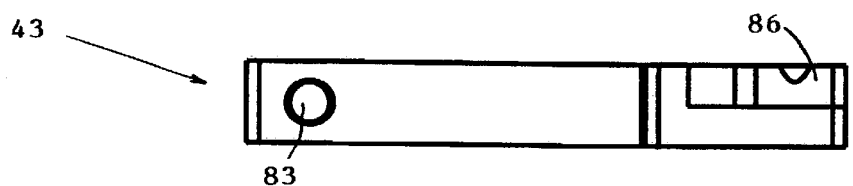
FIG. 18
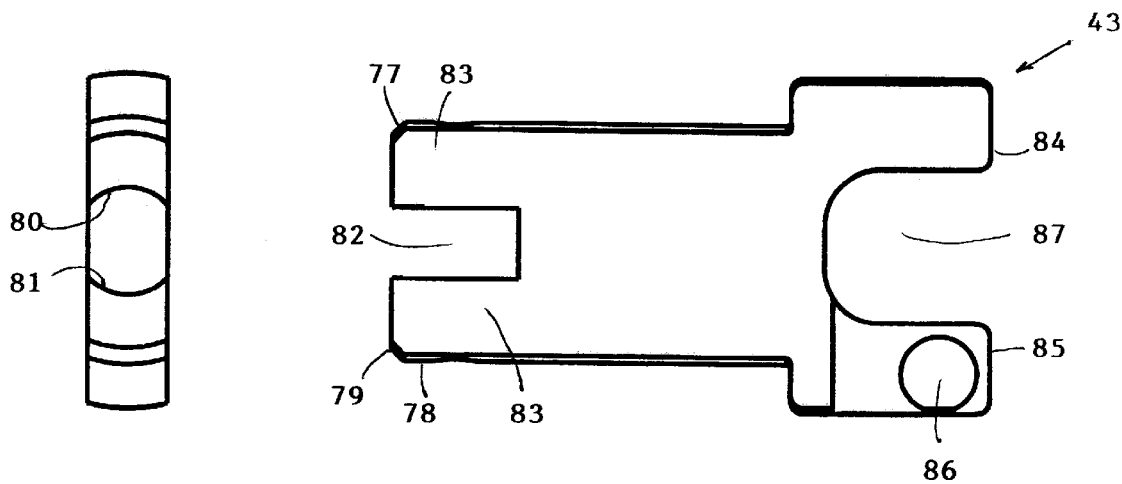
FIG. 19   FIG. 17

LAPAROSCOPIC INSTRUMENT WITH PARALLEL ACTUATED JAWS

BACKGROUND OF THE INVENTION

1. Field of the Invention

The present invention relates to minimally invasive surgical instruments, and more particularly, to instruments having a linkage mechanism and assembly for enabling an end effector, such as jaws of a surgical forceps, to move between an open and a closed position in parallel relationship to each other.

2. Description of the Prior Art

Laparoscopic procedures have been developed relatively recently as a less invasive alternative to traditional open surgeries. Numerous surgical procedures, such as gall bladder operations, are currently performed by laparoscopic techniques. These surgeries are generally termed "minimally invasive surgery" (MIS) and the present invention refers to a class of devices that have rigid shafts with hand-operated handles at one end and an end effector mechanism (such as jaws) at the other end. End effector mechanisms refer to the portion of the surgical instrument that actually contacts and manipulates tissue in a patient. The prior art of most concern herein relates to grasping forceps, which grasp but do not intentionally cut or puncture tissue; for example forceps with broad jaws are use for tasks such as pulling out gall bladders that have been surgically cut away from the liver. These devices replace the surgeon's hands in the traditional open surgery. However, prior laparoscopic grasping devices often may cause problems in their inability to properly grasp the object, such as a gallstone. The lack of satisfactory holding power of these instruments can complicate the surgeon's work. Tissue that must be manipulated during a surgical procedure can have widely varying surface characteristics and can be highly slippery and difficult to grasp. Additionally, such prior devices lack the necessary holding power, thereby forcing the physician to exert significant grasping pressure in order to manipulate tissue as required to perform the surgical procedure. Use of such high grasping pressures can result in increased long-term trauma to the tissue.

The typical instrument employed in laparoscopic surgery has a hollow clindrical shaft, which includes a solid actuating rod. The rod is connected at the distal end to the effector mechanism (jaws), and at the proximal end to one member of the handle assembly. When the handle is operated, the rod slides through the shaft and actuates the end effector mechanism. Serrations and other features (depending on the use for which the instrument is intended) enable the end effector to perform various surgical functions, such as gripping.

Many creative linkages have been devised for converting the surgeon's manual efforts, at the handle end of the instrument, into opening and closing of the instrument's jaws. Typically, although with some exceptions, the handle has a stationary member rigidly joined to a hollow shaft and a movable member pivotally joined to an actuator rod that is mounted and is capable of reciprocal movement within the shaft. When the surgeon squeezes the stationary and movable handle members together, the actuating rod acts upon the jaws (to which it is rotatively fastened by pins, or by tracks of levers kinematically equivalent to pins) in such a way as to make the jaws close. When the surgeon spreads the stationary and movable members apart, the movements are reversed and the jaws open. The jaws are usually attached to the end of the shaft by known means, e.g., by pins or kinematically equivalent tracks. In some cases, levers or other intermediate pieces are interposed between the actuating rod and the jaws for causing the latter to open and close in response to relative movement of the stationary and movable handle members.

When operating the jaws of typical instruments as described above, surgeons have experienced difficulty in grasping slippery tissues because the jaws close first at their rear ends, and thereby tend to propel or push the tissues out from between the jaws. This is illustrated in FIG. 1, which shows that when attempting to grasp a relatively large object, the rotary force tends to push the object out of the jaws as well as hold it. Consequently, trauma of the tissue may result from repeated and increasingly aggressive attempts to grasp the tissue.

Laparoscopic instruments intending to simplify operative treatment on a tissue are known in a large number of variants, particularly when designed as a grasping instrument. Thus U.S. Pat. No. 5,318,589 issued to Lichtman on Jun. 7, 1994, teaches of a surgical instrument having jaws opening and closing. This patent is typical of a class wherein the jaws are normally biased in one position, then moved in response to the squeezing motion of the handle assembly. There is no independent linkage to control the jaws, therefore these jaws will have a tendency to lack grasping power.

U.S. Pat. No. 5,728,121 issued to Bimbo et al. on Mar. 17, 1998, discloses a surgical gripping wherein the grasping jaws employ a gripping material for enhanced holding power. The jaws themselves have a conventional means for movement.

U.S. Pat. No. 5,368,606 issued to Marlow et al. on Nov. 29, 1994, illustrates a means of actuating the jaws by a linkage method of manipulation. The method falls short of teaching a means for opening and closing the jaws in parallel relationship to one another.

U.S. Pat. No. 5,853,412 issued to Mayenburger on Dec. 29, 1998, teaches the use of toggle lever elements to move the jaws. No disclosure is made as to moving the jaws in a parallel relationship to each other.

U.S. Pat. No. 5,308,358 issued to Bond et al. on May 3, 1994, discloses a double-motion actuator assembly which comprises a linkage means, but not a teaching of parallel movement between the jaws themselves.

None of the above inventions and patents, either singly or in combination, is seen to describe the instant invention as claimed.

SUMMARY OF THE INVENTION

Accordingly, the above problems and difficulties are obviated by the present invention which provides for a laparoscopic instrument having an improved surgical gripping for a variety of tissue types at minimal grasping pressures.

More particularly, the instrument of the present invention is comprised of a handle assembly, an elongated laparascopic shaft assembly extending from the handle assembly, and an end effector mechanism being supported on a distal end of the shaft assembly. The end effectors actuate between open and close position by movement of a movable loop handle which pivots in relation to a stationary loop handle. The end effector mechanism includes a pair of opposed cooperating jaw members which are adapted and configured so as to keep the jaws parallel to each other through their range of motion. To accomplish this, a mechanically controlled linkage system is connected to the jaws to maintain the jaws in substantially parallel relationship to each other while the jaws are being opened and closed.

Preferably the shaft assembly is provided with a tubular sheath having a co intensive actuator rod which coaxially reciprocates within it; such that the handle assembly is operationally interconnected to the jaws. The actuator rod is attached to the movable handle, while the sheath is secured to a barrel portion which extends from the stationary handle. As the movable handle pivots, the actuator rod slidably reciprocates within the sheath to open and close the jaws.

The main object of the present invention provides a linkage system that will maintain the jaws parallel to each other, or at a known fixed angle to each other, throughout their range of motion.

Another object of the present invention is to provide jaws with enhanced gripping power without the need of excessive grasping pressure.

Still another object of the present invention is to provide a laparoscopic instrument having jaws that are less traumatic in retracting organs and tissue.

Yet still another object of the present invention is to provide a jaw and linkage system configuration that can be used for a variety of applications which require an improved extended reach grip.

An object of the present invention is to overcome the inherent difficulties which surgeons experience when attempting to manipulate organs, such as gall bladders, filled with gallstones and calcified tissue, which exhibit the "bar of soap effect" when being grasped.

These and other objects of the present invention will become readily apparent upon further review of the following specification and drawings.

BRIEF DESCRIPTION OF THE DRAWINGS

The foregoing objects and other features of the invention will become readily apparent and may be understood by referring to the following detailed description of an illustrative preferred embodiment of the laparoscopic surgical instrument having a novel end effector mechanism, wherein the grasping jaws are maintained in parallel position in respect to each other throughout their range of motion.

FIG. 16 is a pictorial view of the translation member.

FIG. 17 is a longitudinal side view of the translation member.

FIG. 18 is a top view of the translation member as shown in FIG. 17.

FIG. 19 is an end view of the translation member of FIG. 17.

DETAILED DESCRIPTION OF THE PREFERRED EMBODIMENT

Figure 1:
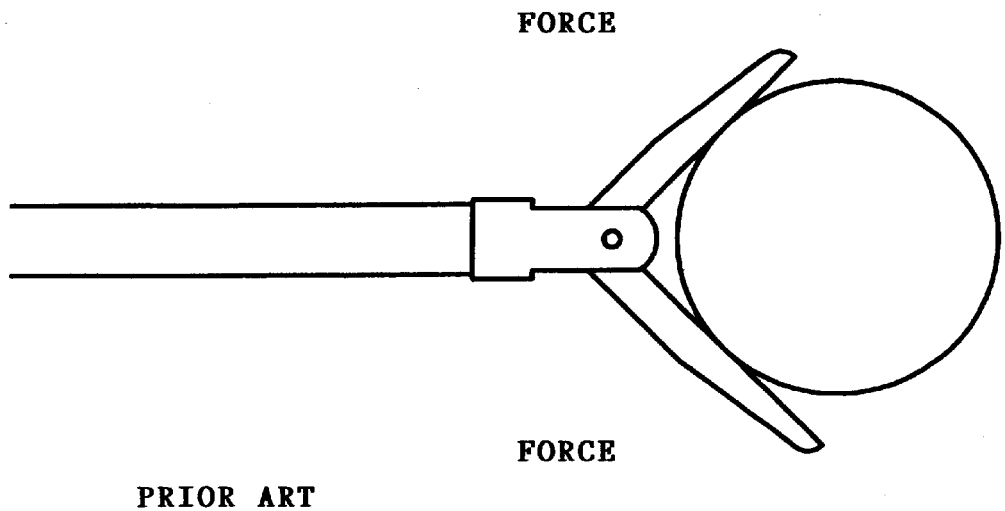
FIG. 1 is a sketch of the typical direction of force that is applied in most of the prior art.
Figure 2:
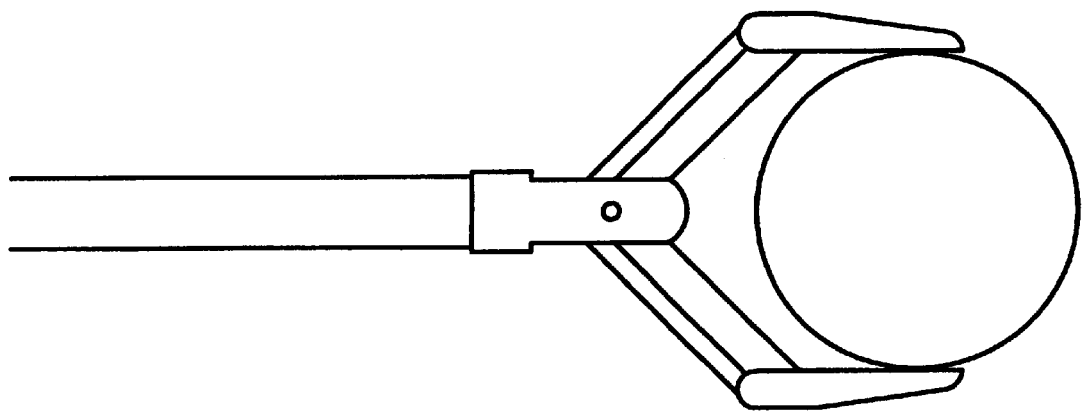
FIG. 2 is a sketch illustrating the direction of the applied gripping forces of the present invention.

A major difficulty facing surgeons performing certain laparoscopic procedures concerns the amount of grasping force required to accomplish the task, yet being careful so as to not overexert the gripping pressure which may harm the tissue. An example would be in the removal of tissue such as a gallbladder filled with calcified gallstones, which can be extremely slippery and therefore difficult to grasp. This is illustrated in the prior art of FIG. 1. The present invention, as presented in FIG. 2, seeks to place the gripping force in a perpendicular direction to longitudinal, which will afford a maximum grasping force with a minimum of gripping pressure.

A laparoscopic instrument 25 according to the present invention, as shown in FIGS. 3–21, comprises a handle assembly 30, an end effector mechanism 31 and an elongated shaft assembly 32 interposed therebetween.

Figure 3:
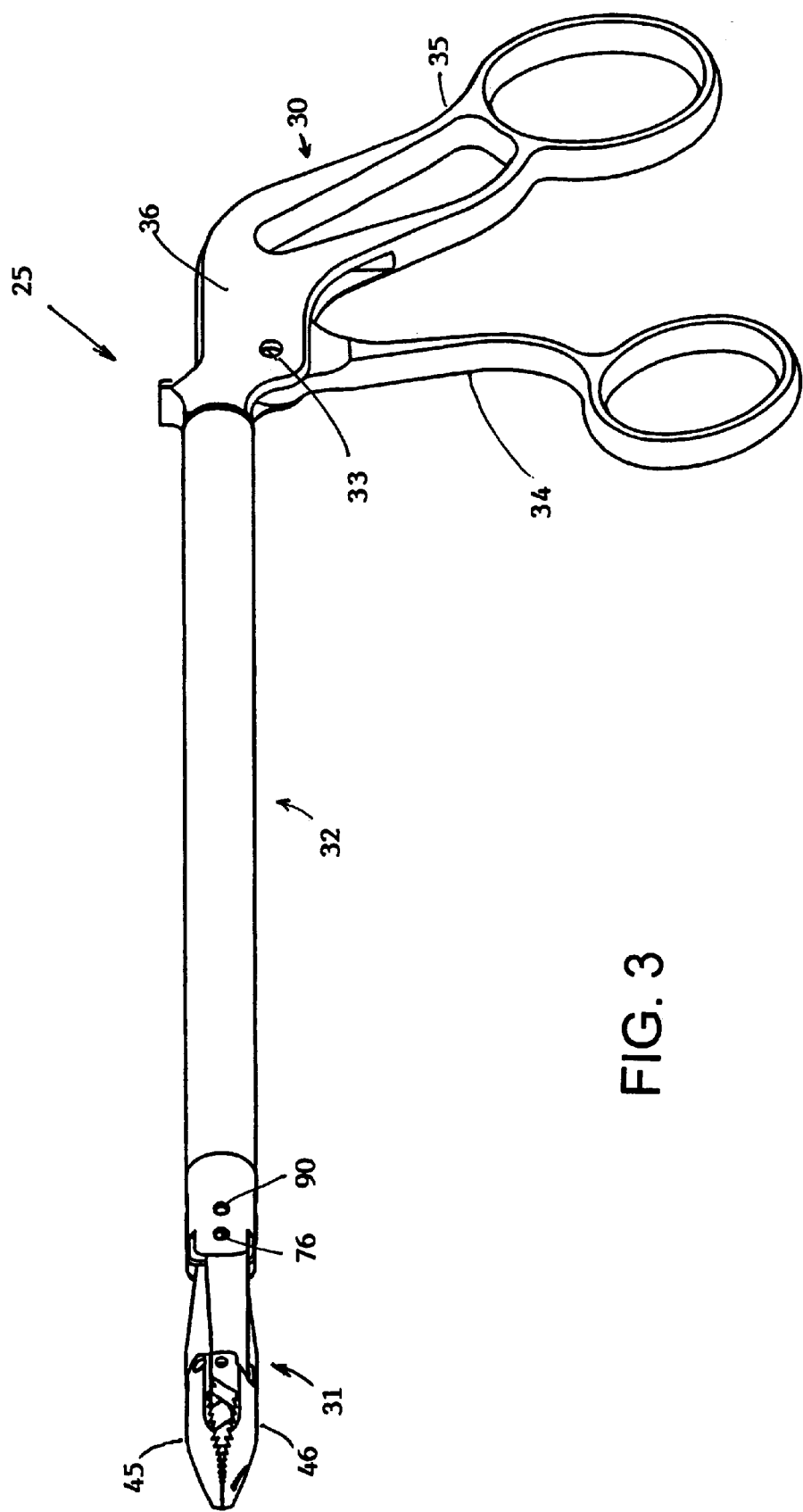
FIG. 3 is a perspective view of the surgical instrument of the present invention.
Figure 4:
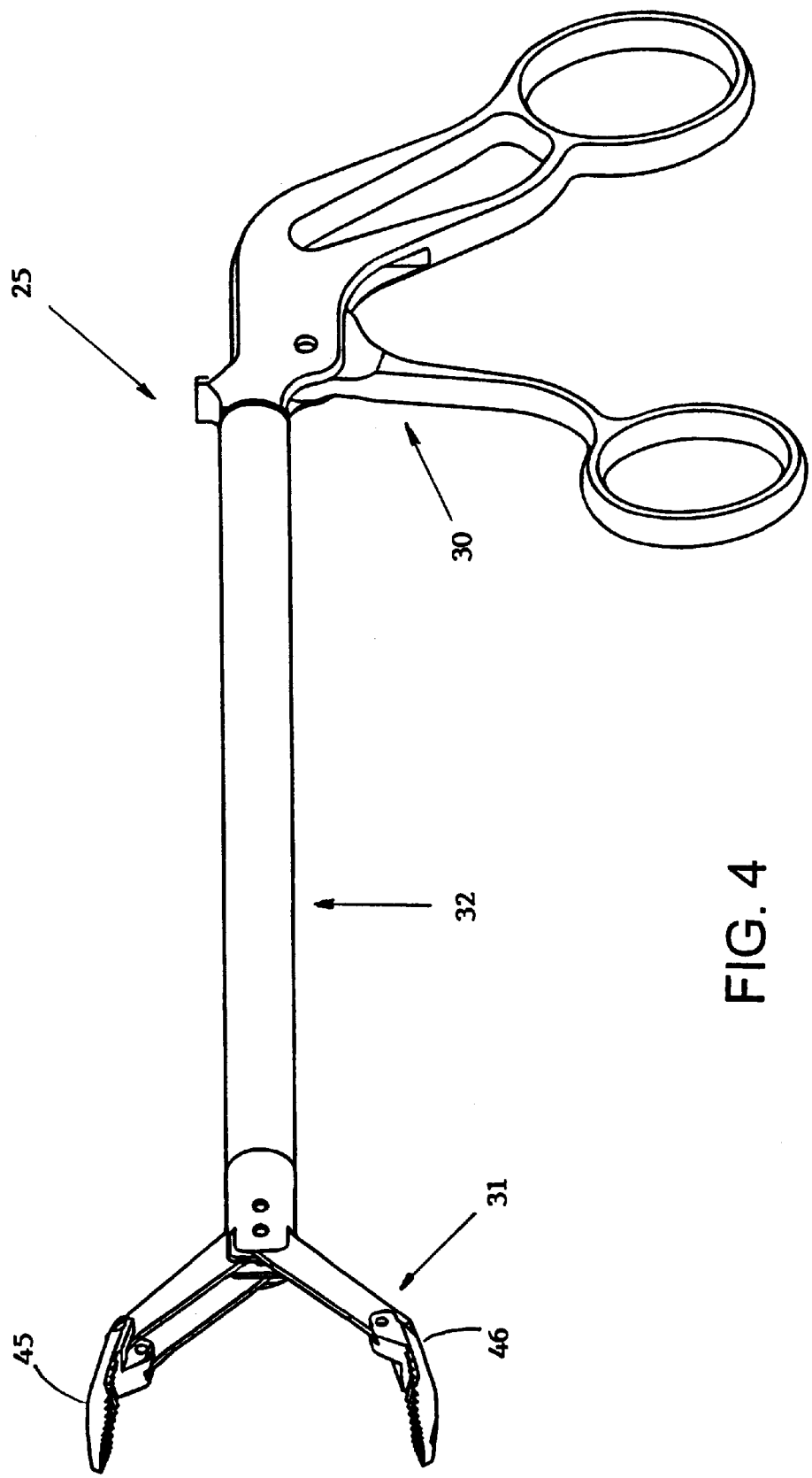
FIG. 4 is a perspective view of the surgical instrument shown in FIG. 3 with the end effector jaws in a fully deployed position.
Figure 5:
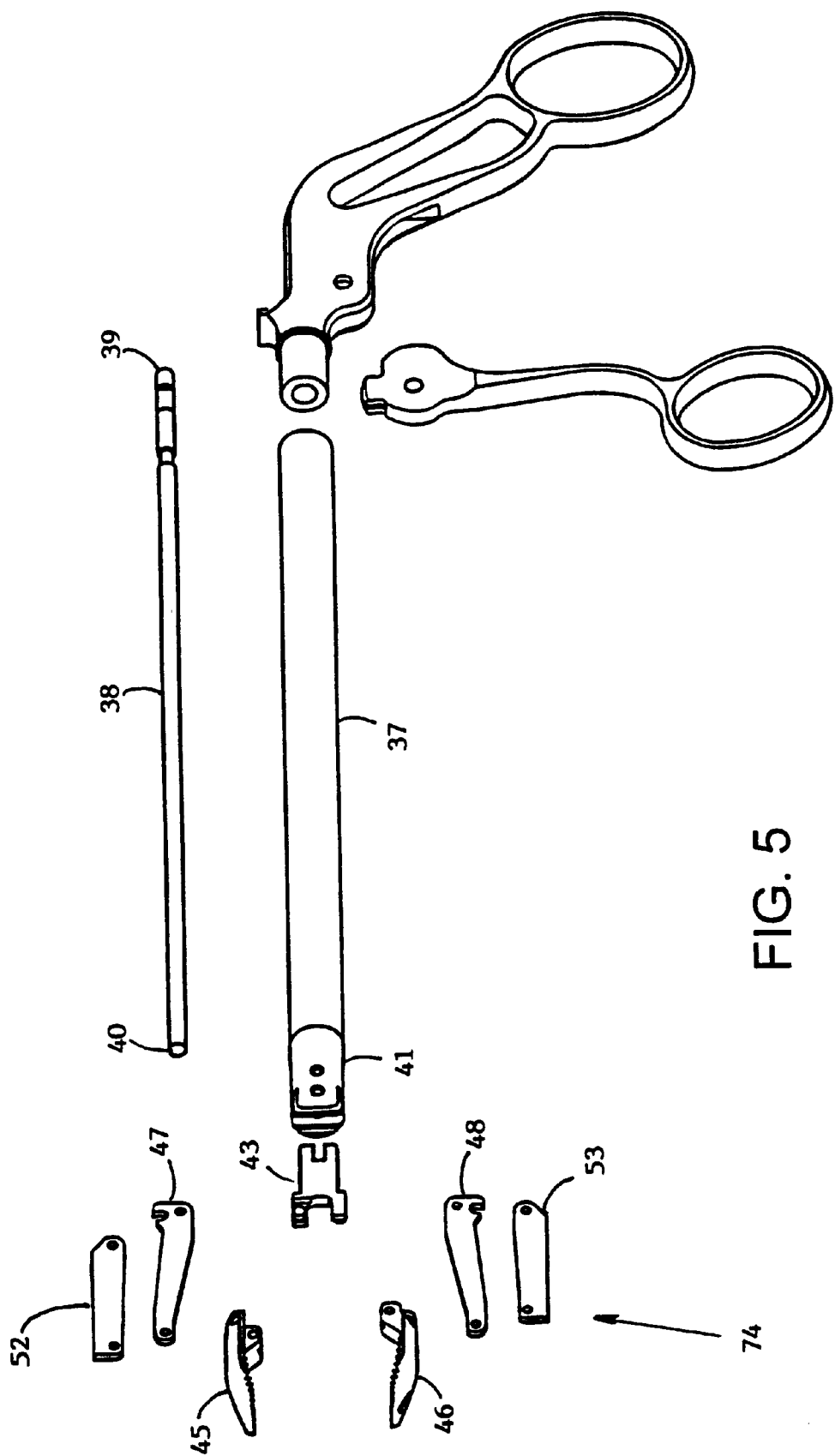
FIG. 5 is an exploded view of the surgical of the present invention.
Figure 7:
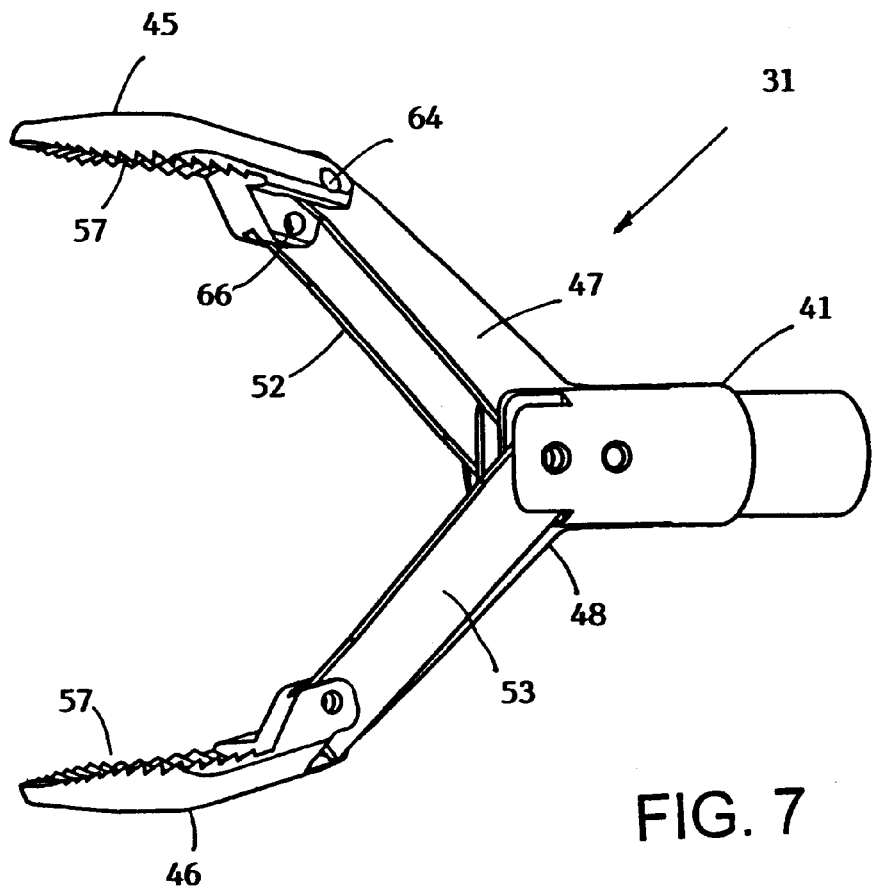
FIG. 7 is a perspective view of the jaw section with the jaws fully deployed.
Figure 6:
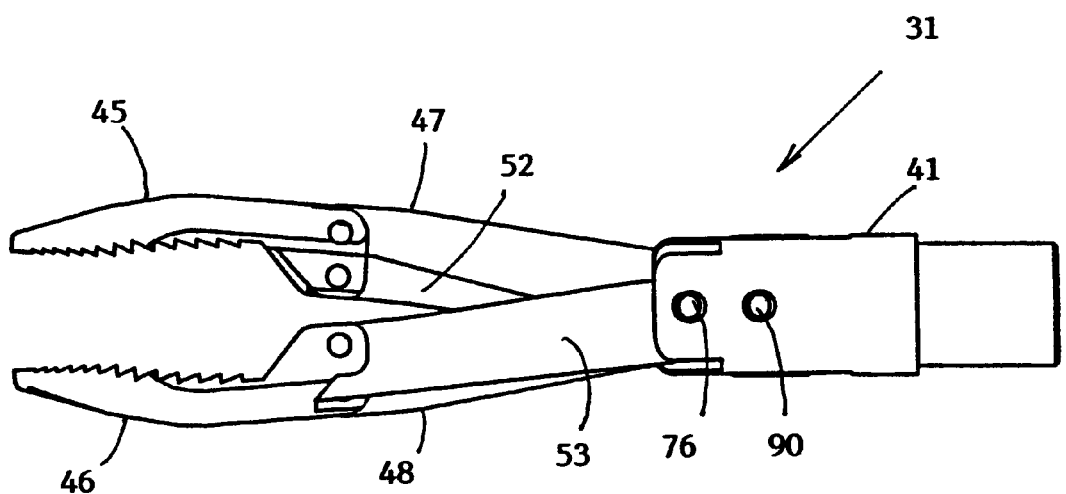
FIG. 6 is a side elevational view of the present invention with jaws in a nearly closed position.
Figure 9:
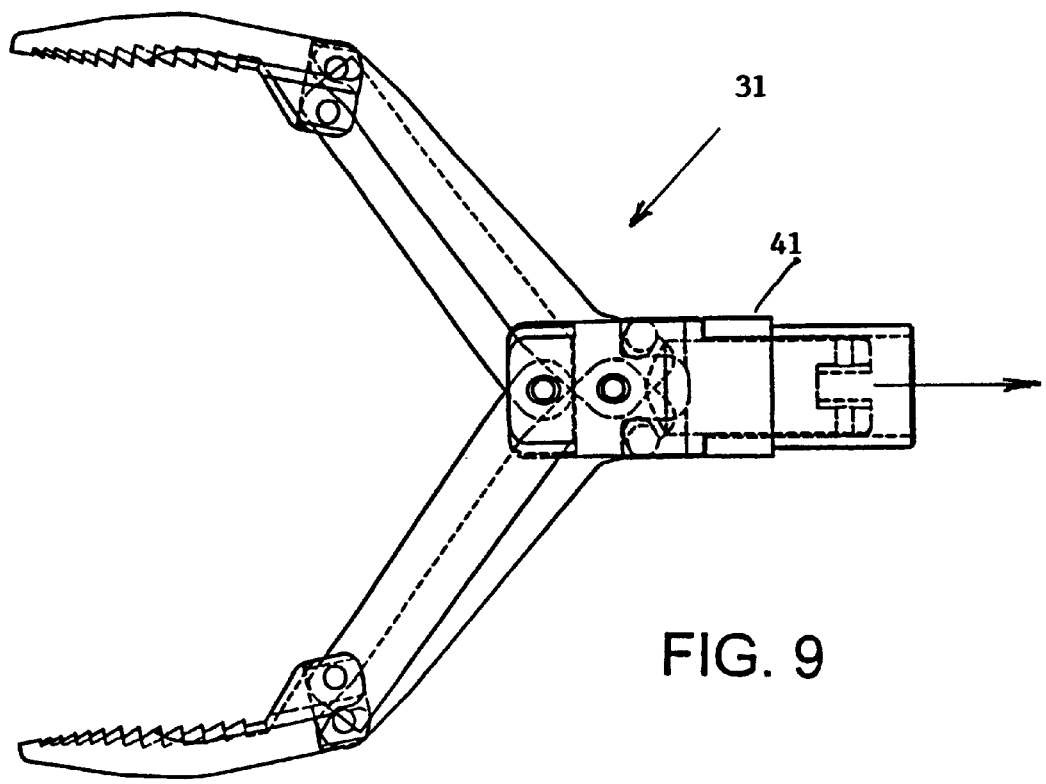
FIG. 9 is a side cross-sectional view of FIG. 7.

As illustrated in FIGS. 3–5, the handle assembly 30 comprises a pivot 33 (which can be a conventional screw, pin or rivet) that holds together a movable loop handle component 34 and a stationary loop handle component 35, which interact in a manner comparable to scissor handles. Stationary handle 35 being of a continuous piece that terminates in a barrel portion 34 which is substantially hollow and is connected to the distally extending shaft assembly 32 by conventional means that are well known to those skilled in the art.

The shaft assembly 32 is established by an outer hollow sheath 37 and a solid coaxial internal actuation rod 38. Rod 38 having a proximal end 39 [Any reference herein to proximal or rear assumes that the handle assembly 30 is at the proximal or rear end of the instrument, any reference to forward or distal assumes the opposite] attached to a conventional type clevis connection (not shown) within barrel portion 36. Actuation rod 38 is adapted to reciprocate coaxially within hollow sheath 37 in response to manipulation of movable handle component 34 by the user, thereby activating end effector mechanism 31.

End effector mechanism 31 of the present invention, as shown in FIGS. 5–9 comprises: a front end housing 41 with a rear end portion 42 connected to a distal end 40 of the sheath 37; a translation member 43 which is reciprocally disposed within a cavity 44 of the front end member 41 having means (to be discussed in detail below) for being longitudinally and coaxially connected to actuation rod 38; a pair of grasping jaw members, a first jaw member 45 and a second jaw member 46, each jaw member a mirror image of the other; and a linkage assembly comprising of: a pair of toggle links, a first toggle link 47 and a second toggle link 48, each toggle link having a proximal end 49 pivotally anchored to the front end member 41, and also at each proximal end 49 a linking yoke 50 rotatively engaging the translation member 43, each toggle link 47 and 48 having a forward end 51 pivotally connected to one of jaw members 45 or 46; and a pair of stabilizing links, a first stabilizing link 52 and a second stabilizing link 53, each stabilizing link having a proximal end 55 pivotally anchored to front end housing 41 and a forward end 54 pivotally connected to one of jaw members 45 or 46. All the above members of end effector mechanism 31 work in coordination to translate the manipulation of handle assembly 30 by the user to operatively open or close jaw members 45 and 46 in a parallel relationship to each other throughout their range of motion, as will be detailed below.

As illustrated in FIGS. 6–9 and 10–12, jaw members 45 and 46 each has an elongated body portion 56, the underside of which comprises a serrated surface 57 for grasping an organ or tissue. The rear end 58 of each jaw member 45 and 46 comprising of an vertically extending upper arm 59, a vertically extending lower arm 60, whereby the arms 59 and 60 therein straddle a central support extension 61 to define an upper slot 62 and a lower slot 63 respectively. The upper slot 62 of each jaw member 45 or 46 pivotally receiving the forward end 51 of one of the corresponding toggle links 47 or 48. An upper pivot pin 64 aligning a hole 65 in the upper arm 59 with an opening 68a in the forward end 51 of one of the toggle links 47 or 48 to pivotally secure the toggle links 47 and 48 to respective jaw members 45 and 46. Lower slot 63 of each jaw member 45 or 46 pivotally receiving the forward end 54 of one of the corresponding stabilizing links 52 or 53. Lower pivot pin 66 aligning a hole 67 in the lower arm 60 with an opening 69b in the forward end 55 of stabilizing link 52 or 53 to pivotally secure stabilizing links 52 and 53 to respective jaw members 45 and 46.

Figure 20:
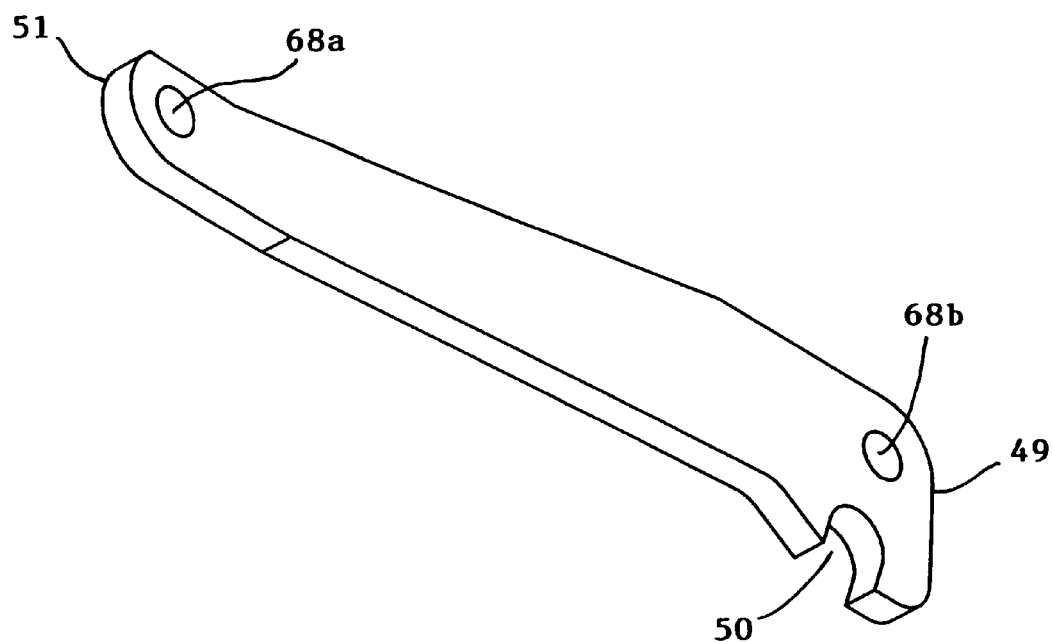
FIG. 20 is a perspective view of the toggle link.
Figure 21:
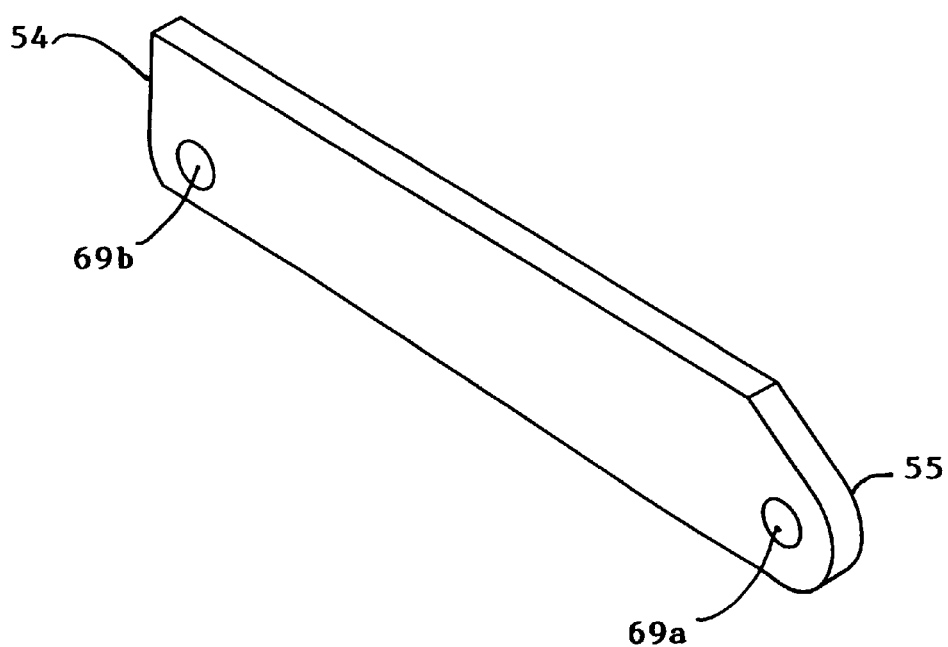
FIG. 21 is a perspective view of the stabilizing link.

As shown in FIGS. 5–9 and 13–15, the rear end portion 42 of front end housing 41 has a generally cylindrical housing and contains the previously mentioned hollow cavity 44 to slidably house translation member 43. The rear portion 42 is press-fitted into the distal end of sheath 37, thereby connecting end effector mechanism 31 to the instrument 25. The forward section of the front end assembly 41 having a yoke-like structure comprising of a pair of support flanges, a first support flange 70 and a second support flange 71. Flanges 70 and 71 extending outwardly and being spaced apart in a generally parallel relationship to one another, wherein an elongated vertically oriented channel 72 is defined. Each of the flanges 70 and 71 having a generally rectangularly shaped recess 73 and 74, of sufficient size to slidably engage the proximal end 55 of each corresponding stabilizer link 52 and 53. Flanges 70 and 71 further having apertures 75 with cooperating flange pivot pins 76 aligning the coordinating apertures 72 with the openings 69a in stabilizer links 52 and 53 to pivotally anchor the stabilizer links 52 and 53 to front end housing 41. The toggle links 47 and 48, as illustrated in FIG. 20, each having an opening 68b in the proximal end 49 which align with orifices 89 in the flanges 70 and 71 whereby a center pin 90 pivotally anchors the toggle links 47 and 48 to the front end housing 41. The aforementioned arrangement thereby prevents any linear movement of the links 47, 48, 52 or 53 with respect to front end housing 41.

FIGS. 6–9 and 16–19 depict the translation member 43 as slidably disposed in cavity 44 of front end housing 41. A pair of rod supports, an upper support 77 and a lower support 78, extend outwardly from the rear end portion 79 of translation member 43, with support 77 in a position above support 78. The circular inner surfaces 80 and 81 of rod supports 77 and 78 define an open-sided sleeve 82, which is of sufficient diameter to engage actuation rod 38. Rod supports 77 and 78 have rivet openings 83 defined therein for passage of a rivet (not shown) for aligning rivet openings 83 with a similar size opening (not shown) in actuation rod 38, to fixedly secure rod 38 to translation member 43, whereby axial reciprocation of rod 38 by handle assembly 30, will subsequently translate a similar longitudinal reciprocating movement to translation member 43. The forward end of translation member 43 having a pair of ears, a first ear 84 and a second ear 85 which project outwardly, each having a yoke pin 86 integrally mounted on the respective exterior surface 91 and 92. The interior surfaces defining a groove 87 which is adapted to allow for passage of the center pin 90. As previously stated, the proximal ends 49 of toggle links 47 and 48 have linking yokes 50 defined therein which rotatively connect with yoke pins 86, whereby linear motion of actuation rod 38 is translated into mainly vertical motion to jaw members 45 and 46, wherein they either open or close in response to the manipulation of handle assembly 30 by the surgeon.

Figure 8:
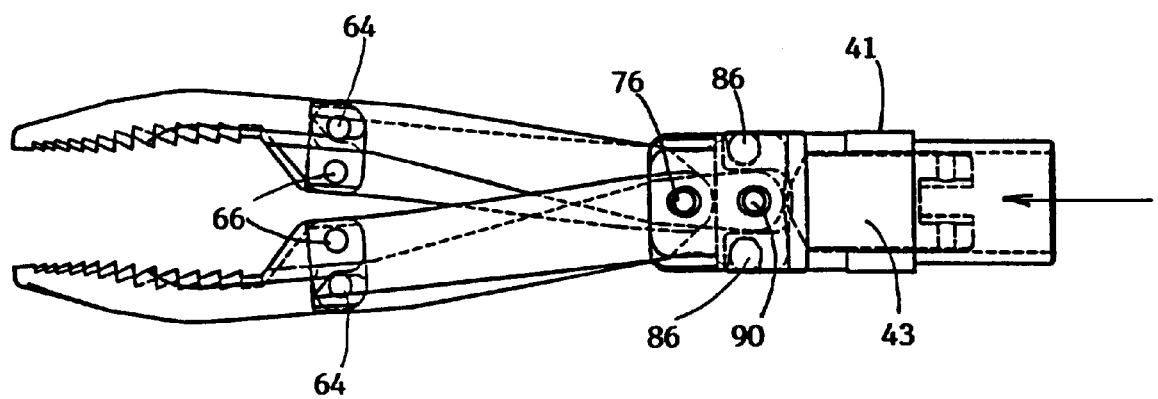
FIG. 8 is a side cross-sectional view of FIG. 6.
Figure 10:
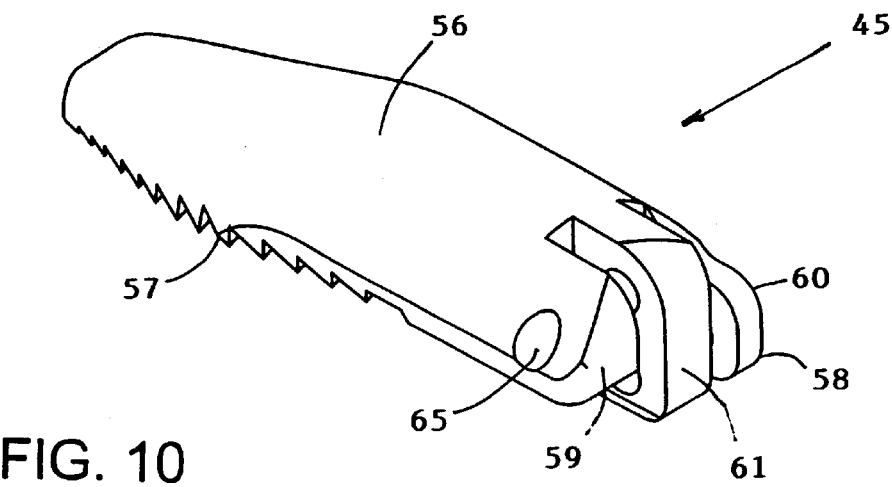
FIG. 10 is a pictorial view of one of the jaw members.
Figure 12:
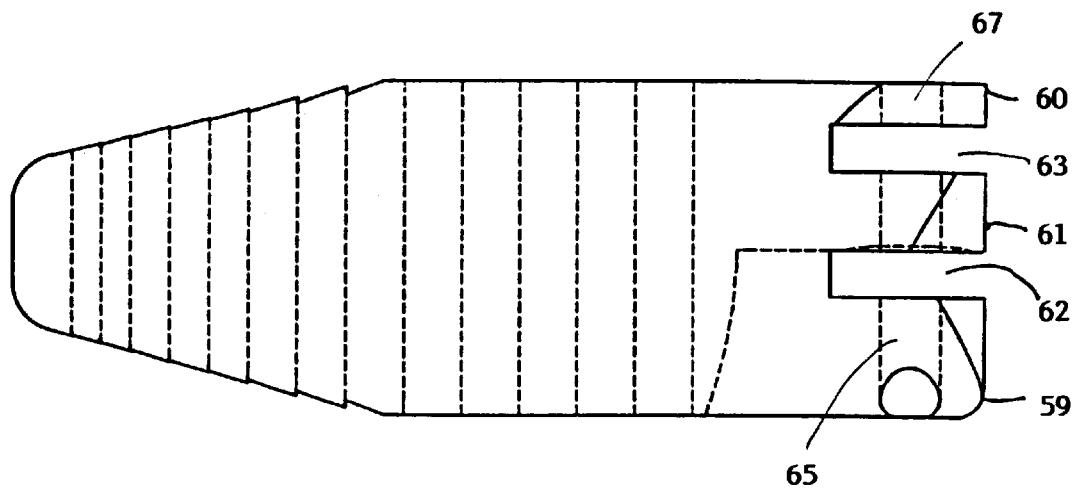
FIG. 12 is a top view of the jaw member shown in FIG. 11
Figure 11:
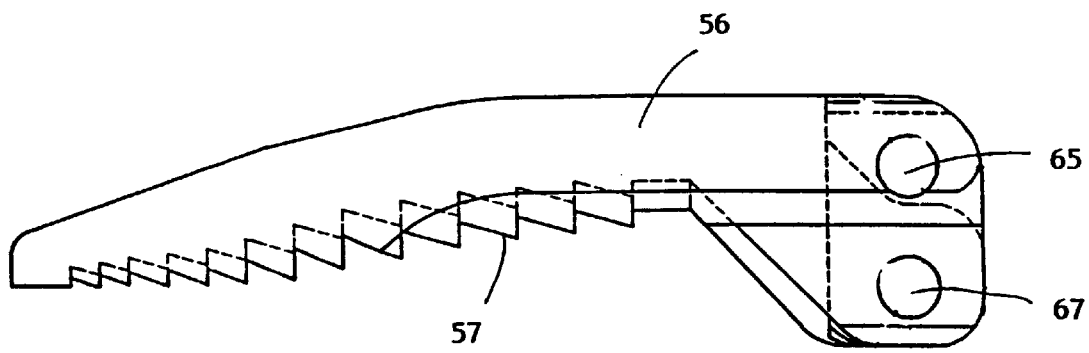
FIG. 11 is a longitudinal side view of the jaw member.
Figure 13:
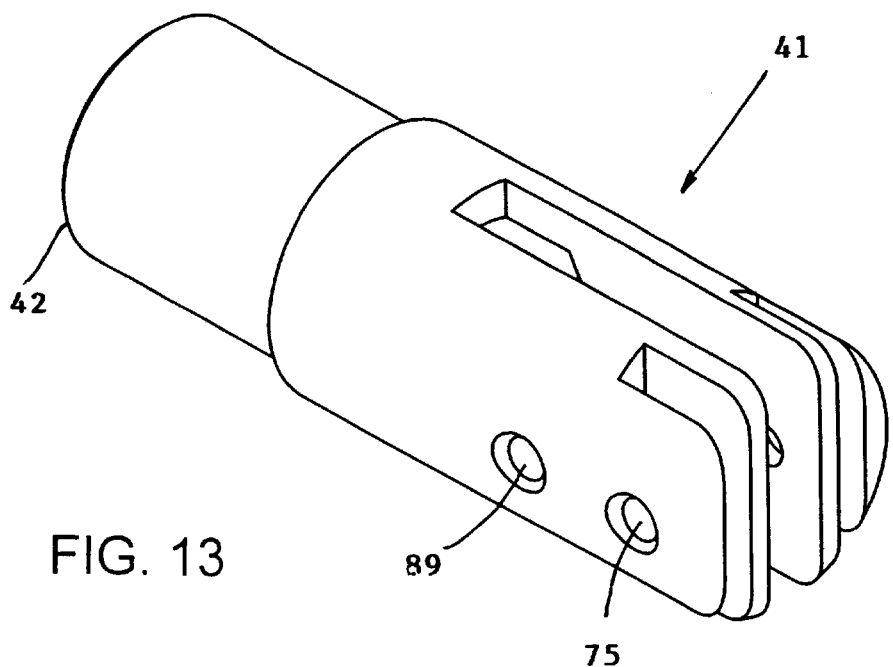
FIG. 13 is a pictorial view of the front end member.
Figure 15:
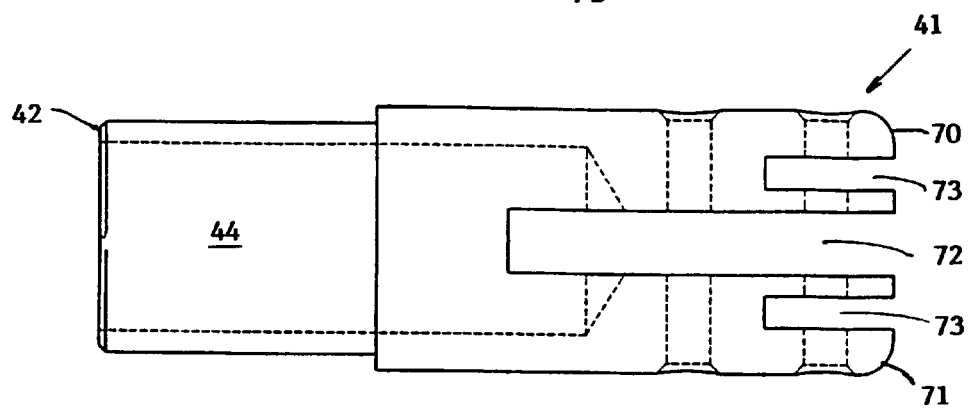
FIG. 15 is a top view of the front end member as shown in FIG. 14.
Figure 14:
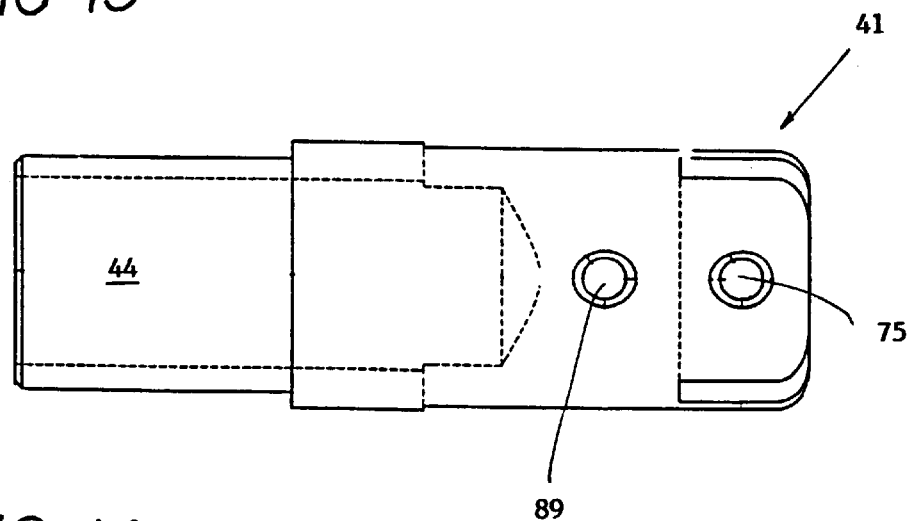
FIG. 14 is a longitudinal side view of the front end member.

The novel feature of instrument 25 is in the manner in which the mechanically controlled linkage assembly 74 causes jaw members 45 and 46 to either open or close. Transmission of actuation forces from actuation rod 38 to the jaws 45 and 46 is shown schematically in FIGS. 8 and 9. When the actuation rod 38 and therein translation member 43 are pulled backward (i.e., toward the handle) by separating handle 34 relative to handle 35, approximately as shown by the arrow in FIG. 9, toggle links 47 and 48 rotate about yoke pins 86, thereby causing them to be pivoted about the center pin 90 wherein the jaw members 45 and 46 to be pushed toward an open position, which allows them to engulf a piece of tissue. Reversing the process by squeezing the handle 34 relative to handle 35, as shown in FIG. 8, causes toggle links 47 and 48 to close respective jaw members 45 and 46 to securely grip the piece of tissue. Stabilizing links 52 and 53, each being pivotedly connected at their proximal end 55 to the front end housing 41 and at their forward end 54 to one of the jaws 45 or 46, pivot upon rotative movement of toggle links 47 and 48. It is a function of the geometric placement of the upper and lower pivot pins 64 and 66 of each jaw member 45 and 46, in relationship with the flange pivot pins 76 of each flange 70 and 71 with the center pivot pin 90 that maintains the necessary geometric configuration and distance between the toggle links 47, 48 and respective stabilizing links 52, 53, such that jaw member 45 is kept in a substantially parallel position to jaw member 46.

While this invention has been primarily shown and described with reference to the preferred embodiment thereof, it will be understood by those skilled in the art that various changes in form and details may be made therein without departing from the spirit and scope of the invention as defined by the appended claims.

LEGEND

25 Instrument
30 Handle Assembly
31 End Effector Mechanism
32 Shaft Assembly
33 Pivot
34 Movable loop handle component
35 Stationary loop handle component
36 Barrel portion
37 Hollow Sheath
38 Actuation rod
39 Proximal end of Actuation rod
40 Distal end of Actuation rod 41 Front End Housing
42 Rear End Portion of Front End Member
43 Translation member
44 Cavity in Front End Member
45 First Jaw Member
46 Second Jaw Member
47 First Toggle Link Element
48 Second Toggle Link Element
49 Proximal end of Toggle Links
50 Linking Yoke on proximal end of Toggle Link
51 Forward end of Toggle Links
52 First Stabilizing Link Element
53 Second Stabilizing Link Element
54 Forward end of Stabilizing Links
55 Proximal end of Stabilizing Links
56 Elongated body portion of Jaws
57 Serrated surface
58 Rear end of Jaw
59 Upper Arm of Jaw
60 Lower Arm of Jaw
61 Central Support Extension
62 Upper Slot of Jaw
63 Lower Slot of Jaw
64 Upper Pivot Pin
65 Hole in Upper Arm
66 Lower Pivot Pin
67 Hole in Lower Arm
68a Opening in forward end of Toggle Links
68b Opening in proximal end of Toggle Links
69a Opening in proximal end of Stabilizing Links
69b Opening in forward end of Stabilizing Links
70 First Support Flange
71 Second Support Flange
72 Channel
73 Recess in Support Flanges
74 Linkage Assembly
75 Aperture in Flanges
76 Flange pivot pins
77 Rod Support (upper position)
78 Rod Support (lower position)
79 Rear End Portion of Translation Member
80 Curved inner surface of 77
81 Curved inner surface of 78
82 Open-sided Sleeve
83 Rivet Openings
84 First Ear of Actuator Member
85 Second Ear of Actuator Member
86 Yoke Pin
87 Groove
89 Orifices
90 Center Pin
91 Exterior surface of First Ear
92 Exterior surface of Second Ear

I claim:

1. a surgical instrument of the laparoscopic type comprising:
   a) a handle assembly having means for actuating the instrument;
   b) a shaft assembly comprising a hollow sheath and an actuation rod disposed for axial movement within the sheath, wherein the sheath and the actuation rod each have a proximal end and a distal end, the proximal end of the actuation rod reciprocally connected to the actuation means of the handle assembly; and
   c) an end effector mechanism operatively associated with the distal end of the actuation rod, the mechanism comprising:
      a pair of grasping members operable to open and close in parallel face to face relation to each other in response to movement by the handle assembly,
      a front end housing connected to the distal end of the sheath, the front end housing having a cavity defined therein,
      a linkage assembly having means for pivotally interconnecting the jaw members to the front end housing,
      a translation member coaxially disposed within the cavity, having means for reciprocally connecting to the actuation rod and rotatively connecting to the linkage assembly wherein linear motion of the actuation rod is translated to rotational direction in the linkage assembly, whereby the grasping members are adapted to respond to the actuation motion of the handle assembly to thereby open or close the grasping members in parallel relationship to each other throughout their range of motion, and
      the pivotally interconnecting means of the linkage assembly comprises:
         a pair of toggle link elements, each toggle link having a forward end pivotally connecting with the corresponding grasping member, each toggle link having a proximal end for pivotally anchoring to the front end housing, each toggle link further having a linking yoke defined on the proximal end for rotatively connecting to the translation member, whereby linear motion of the translation member will adapt the forward ends of the toggle links to rotate either outwardly or inwardly to either open or close the grasping member; and
         a pair of stabilizing link elements positioned outside of and generally parallel to the toggle links, each stabilizing link having a forward end pivotally connecting to the grasping member, each stabilizing link having a proximal end pivotally connecting with the front end housing, wherein in response to movement by the toggle links, the stabilizing links will pivot in a geometrically controlled manner, thereby maintaining the parallel relationship of the grasping members to each other throughout their movement,
         whereby a retracted actuation by the handle assembly will cause the grasping members to open in a parallel relation to each other, while an extended actuation will cause the grasping members to close.

2. The instrument according to claim 1, wherein the grasping members are jaw members having opposing serrated surfaces.

3. The instrument according to claim 2, wherein the jaw members include a first jaw member and a second jaw member, each jaw member includes:
   a rear end portion having an upper arm, a lower arm and a central support extension;
   the upper arm and central support extension forming an upper slot therebetween, the upper slot being of sufficient width to slidably receive the forward end of one of the toggle links, the upper arm having a pivot pin to pivotally connect the toggle link within the upper slot; and
   the lower arm and central support extension forming a lower slot therebetween, the lower slot having sufficient width to slidably receive the forward end of one of the stabilizing links, the lower arm having a pivot pin to pivotally connect the stabilizing link within the lower slot, whereby each jaw member is pivotally connected to the toggle link which is adapted to urge the jaw either open or closed, and each jaw member is pivotally connected to the stabilizing link which is adapted to maintain the serrated surfaces of the jaws in a parallel relationship to each other.

4. The instrument according to claim 3, wherein for connecting to the sheath the front end housing for connecting to the sheath comprises a cylindrical rear end portion adapted to be press-fitted into the distal end of the sheath.

5. The instrument according to claim 4, wherein the front end housing comprises:
   a forward portion having a pair of generally parallel spaced flanges extending therefrom,
   the flanges having interior surfaces defining a generally rectangularly shaped channel of sufficient size to slidably accept the proximal ends of the toggle link elements, a center pin pivotally anchoring the toggle links to the front end housing;
   the flanges each have a recess defined therein of sufficient width to slidably accept the proximal ends of the stabilizing links, flange pivot pins pivotally connecting the stabilizing links to the front end housing,
   whereby the front end housing pivotally anchors the links to eliminate linear motion therein.

6. The instrument according to claim 5, wherein the means for reciprocally connecting the translation member to the actuation rod comprises a pair of rod supports, an upper rod support and a lower rod support, each rod support extending from a rear portion of the translation member, each rod support having an inner circular surface defining an open-sided sleeve of sufficient diameter to accept the distal end of the actuation rod, each rod support having means for riveting to the actuator member,
   whereby the translation member will reciprocate the linear movement of the activation rod.

7. The instrument according to claim 6, wherein the translation member comprises:
   a pair of ears extending from a forward end,
   a groove defined by the interior surfaces of each ear, to allow room for linear motion of the translation member within the front end housing; and
   a yoke pin integrally mounted on the exterior surface of each ear for rotatively connecting with the linking yoke of the corresponding toggle link element,
   whereby linear motion of the translation member is converted into generally vertical motion by action of the toggle links, such that a retracted linear motion will subsequently cause the jaws to open and an extended linear motion will cause the jaws to close.

8. The instrument according to claim 1, wherein the actuating means of the handle comprises:
   a stationary handle component with an extending barrel portion;
   a movable handle component that is pivotally connected to the barrel portion; and
   the barrel portion having means for connecting to the proximal end of the actuation rod
   whereby the user, upon squeezing the handle components together, will cause the jaw members to close in parallel to each other, and by extending the handle components will cause the jaw members to open.

9. A surgical instrument of the laparoscopic type comprising the combination of:
   a) a handle assembly having a stationary handle with an extending barrel portion, a movable handle that pivots in relationship to the stationary handle for operating the instrument;
   b) a shaft assembly having a hollow sheath and an actuation rod reciprocally and coaxially transposed within the sheath, a proximal end of the actuation rod having means for connecting to the barrel portion of the handle assembly,
   whereby motion of the movable handle will cause the actuation rod to reciprocate in a longitudinal linear movement relative to the sheath; and
   c) an end effector mechanism having:
   a front end housing having a rear end portion press-fitted into a distal end of the shaft assembly, a cavity defined within the housing, a forward section having a yoke-like structure,
   a pair of jaw members for gripping an object,
   a translation member reciprocally transposed with the cavity of the front end housing, means for operatively associating the translation member with the distal end of the actuation rod, the means comprising of a pair of rod supports extending outwardly from a rear end portion, the rod supports having circular inner surfaces defining an open-sided sleeve of sufficient diameter to slidably receive the actuation rod,
   a pair of ears extending from a forward section of the translation member, the ears comprising a first ear and a second ear, the ears each having a yoke pin integrally mounted on its exterior surface, and
   a linkage assembly pivotally connecting the front end housing and yoke pins of the translation member to the jaw members for translating pivotal movement of the handle assembly to the jaw members,
   whereby the jaws will open or close in parallel relationship to each other throughout their range of motion in response to pivotable motion of the movable handle.

10. The instrument according to claim 9, wherein the linkage assembly includes:
    a pair of toggle links, a first toggle link and a second toggle link, each toggle link having a linking yoke defined on its proximal end for rotatively connecting to corresponding yoke pins of the translation member;
    means for pivotally anchoring the proximal end of each toggle link to the front end housing; and
    each toggle link having a forward end for pivotally engaging with one of the jaw members,
    whereby the linear reciprocating motion imparted by the actuation rod is adaptably translated to the yoke pins of the translation member, thereby causing the link yokes of each toggle link to rotatively pivot to either push open the jaws or to pull close the jaws.

11. The instrument according to claim 10, wherein the linkage assembly includes:
    a pair of stabilizing links, a first stabilizing link and a second stabilizing link, each stabilizing link having a proximal end for pivotally connecting with the front end housing, each stabilizing link having a forward end for pivotally connecting to a corresponding jaw member,
    whereby upon rotative movement of the toggle links causing the jaws to either open or close, the geometrical structure and positioning of the stabilizing links prevents the jaws from being able to move in anything but a parallel face to face relationship to each other.

12. The instrument according to claim 11, wherein the jaw members include a first jaw member and a second jaw member, each jaw member includes:

an opposing serrated surfaces for grasping the object:
- a rear portion having an upper arm, a lower arm and a central support extension;
- the upper arm and central support extension cooperating to form an upper slot therebetween, the upper slot being of sufficient width to slidably accept the forward end of the toggle links, the upper arm having an upper pivot pin pivotally connecting the toggle link within the upper slot; and
- the lower arm and central support extension cooperating to form a lower slot therebetween, the lower slot having sufficient width to receive the forward end of one of the stabilizing links, the lower arm having a lower pivot to pivotally connect the stabilizing link within the lower slot,
- whereby each jaw member is pivotally connected to a toggle link which is adapted to urge the jaw members either open or closed, and each jaw member is pivotally connected to a stabilizing link which is adapted to maintain the serrated surfaces of the jaws in a parallel relationship to each other throughout their range of motion.

13. The instrument according to claim 12, wherein the means for affixing the actuation rod to the translation member comprises a rivet passing through the rod supports and actuation rod.

14. The instrument according to claim 12, wherein the means for anchoring the toggle links to the front end housing comprises:
- the forward section of the front end housing having a pair of extending flanges, the flanges defining a channel therebetween of sufficient size to accept the proximal ends of the toggle links, a center pin pivotally anchoring the toggle links within the channel.

15. The instrument according to claim 14, wherein each of the flanges of the front end housing has a recess defined therein of sufficient width to slidably receive the proximal end of one of the stabilizing links, a pivot pin in each flange for pivotally connecting the stabilizing link within the recess.

* * * * *